United States Patent
Schaller

Patent Number: 5,810,864
Date of Patent: Sep. 22, 1998

[54] SURGICAL INSTRUMENT SYSTEM

[76] Inventor: Günter Schaller, Am Lusbüehl 32a, D 79110 Freiburg, Germany

[21] Appl. No.: 708,045

[22] Filed: Aug. 30, 1996

[30] Foreign Application Priority Data

Sep. 3, 1995 [DE] Germany .................. 195 32 453.6

[51] Int. Cl.$^6$ .................................................. A61B 17/00
[52] U.S. Cl. ...................... 606/170; 606/174; 606/180
[58] Field of Search ................................. 606/1, 51, 52, 606/170, 174, 205–210; 128/750–755

[56] References Cited

U.S. PATENT DOCUMENTS

| | | | |
|---|---|---|---|
| 2,790,437 | 4/1957 | Moore . | |
| 3,949,747 | 4/1976 | Hevesy | 128/754 |
| 5,318,589 | 6/1994 | Lichtman | 606/167 |
| 5,407,293 | 4/1995 | Crainich . | |
| 5,472,446 | 12/1995 | de la Torre . | |
| 5,486,185 | 1/1996 | Freitas et al. . | |
| 5,507,774 | 4/1996 | Holmes et al. | 606/205 |
| 5,571,137 | 11/1996 | Marlow et al. | 606/167 |
| 5,630,832 | 5/1997 | Giordano et al. | 606/208 |

*Primary Examiner*—William Lewis
*Attorney, Agent, or Firm*—Jeffrey M. Kaden; Norbert P. Holler; Gottlieb, Rackman & Reisman, P.C.

[57] ABSTRACT

A surgical instrument system for the use in minimal invasive surgery is adaptable to all surgical tasks by interchangeable instrument heads with different surgical tools. The instrument holder includes a handgrip, a tube extending therefrom and a shaft. The shaft is slidably received in the tube and selectively engaged with the trigger handle of the handgrip. At a distal tie-in point different interchangeable instrument heads are connected tensile resistent to the shaft and their function is actuated with the trigger handle via the same shaft. With the aid of a grip member provided at its proximal end, the shaft is operated to set its tie-in points in function.

32 Claims, 9 Drawing Sheets

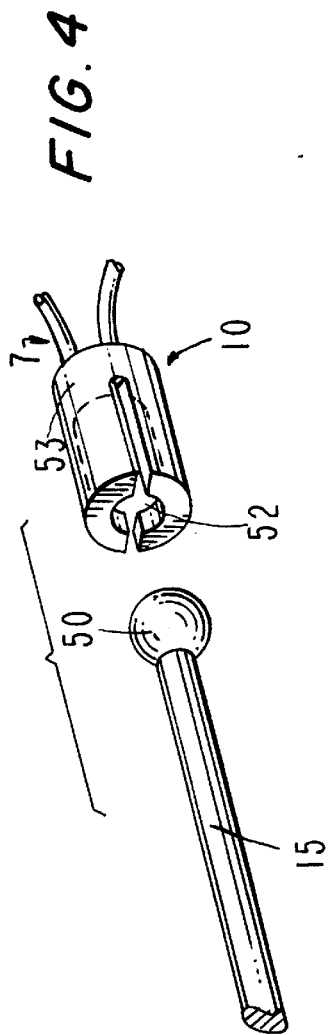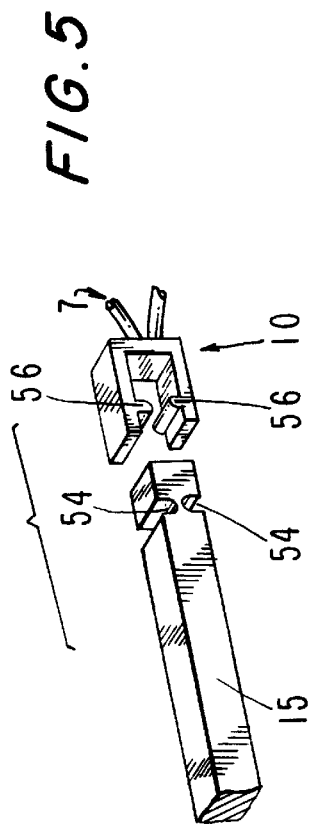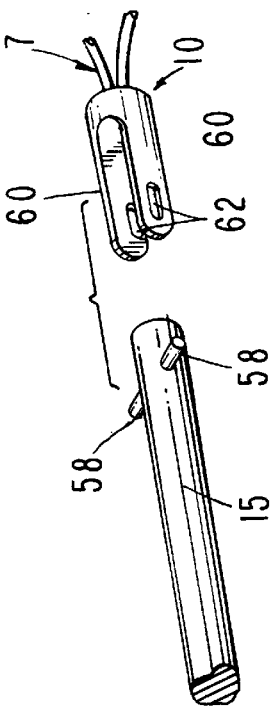

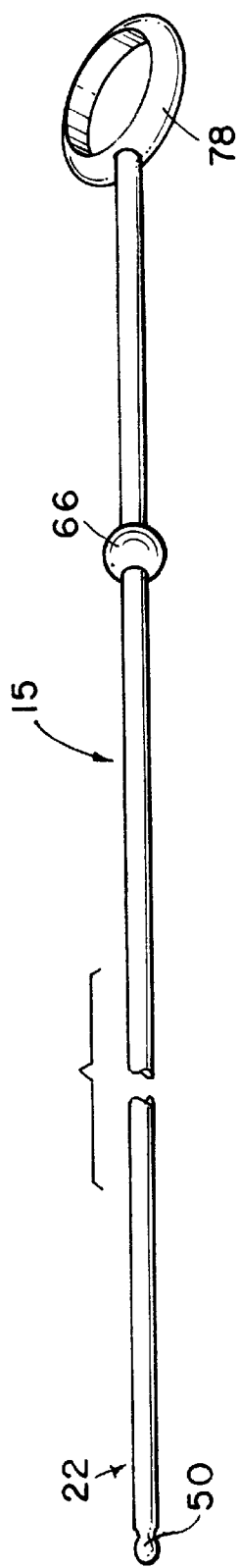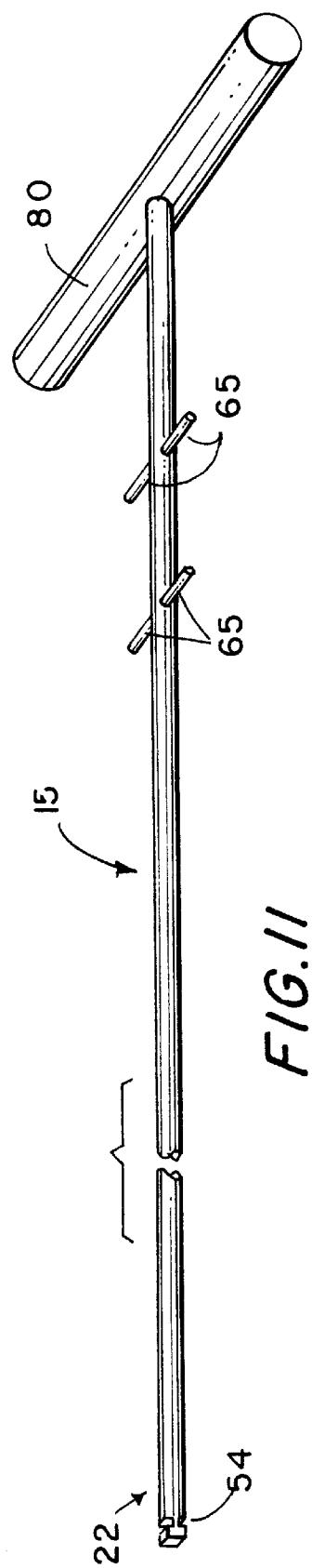

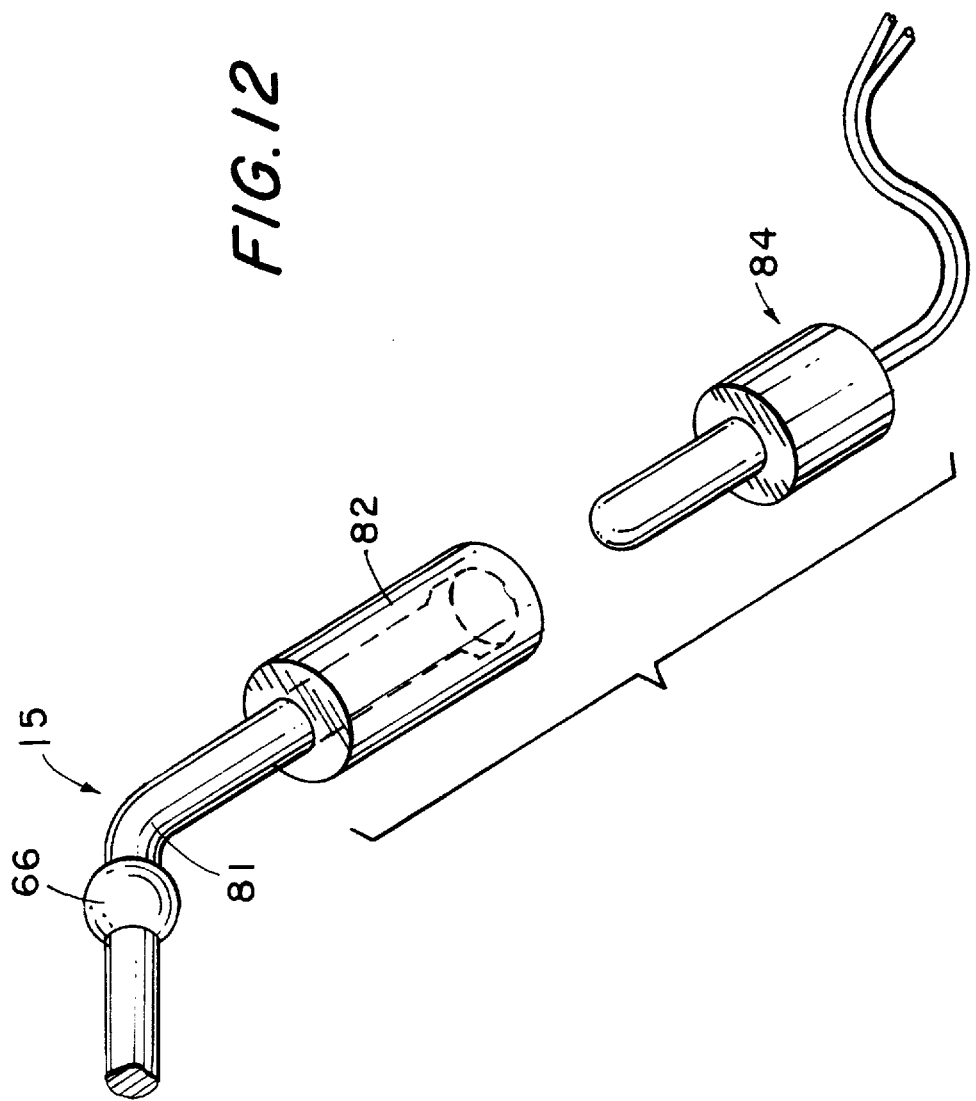

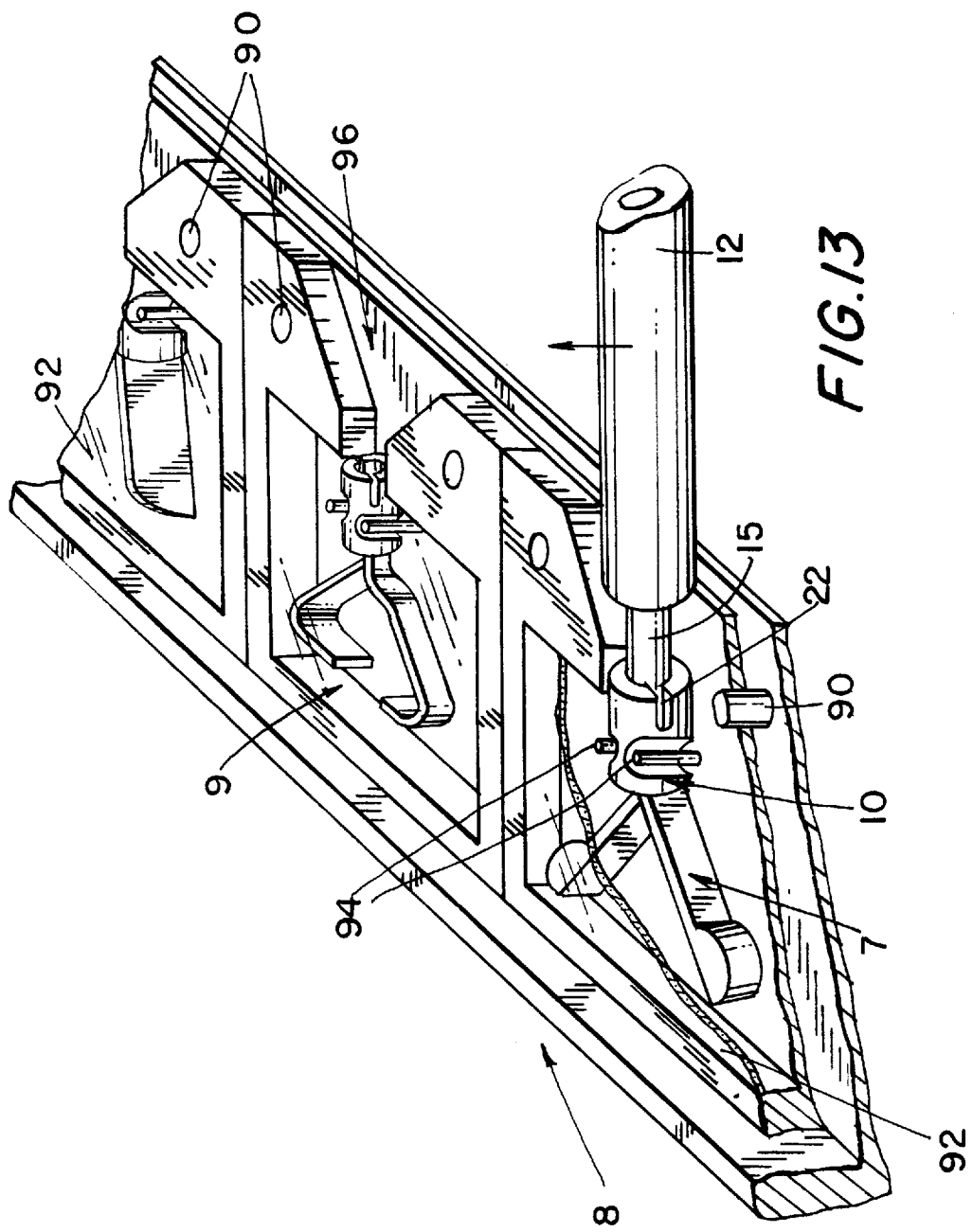

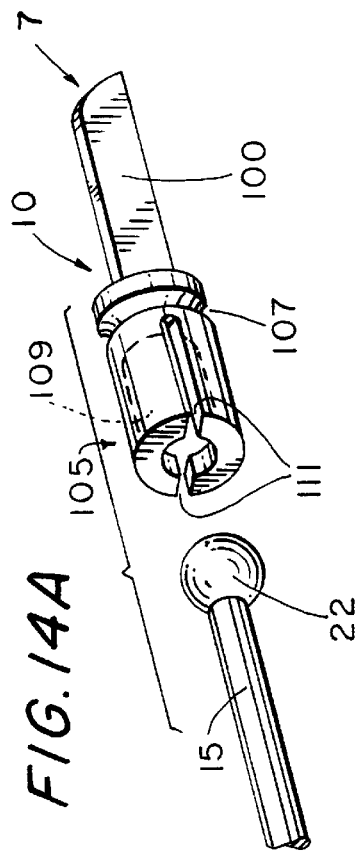
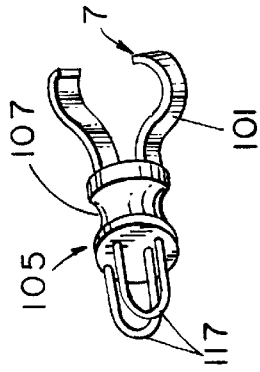
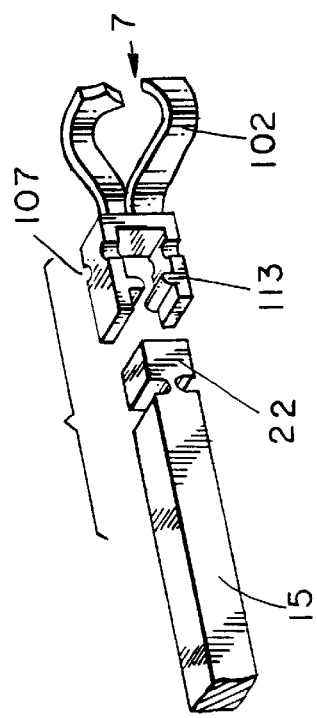
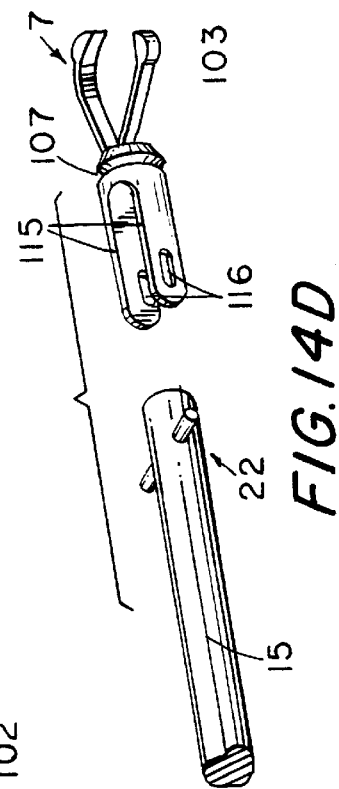

SURGICAL INSTRUMENT SYSTEM

TECHNICAL FIELD

The present invention is in general related to medical devices and more particularly related to an instrument system for use in minimal invasive surgery.

BACKGROUND OF THE INVENTION

Surgical instruments for minimal invasive surgery are known in the art to have a handgrip to hold and actuate the instrument head with a plurality of surgical tools via a rod-like or similar interior drive component, guided in a tube with a small diameter. Minimal invasive surgery e.g. in the abdominal cavity is carried out through a small incision to reduce the trauma of the body and to avoid infection by airborne materials.

All these instruments present identical constructions for holding and actuating the function. The smallest part at the tip defines the instrument functions like grasping, cutting or sealing tissues. For the operation itself, being done under videocontrol in a darkened room, the differentation is difficult with the particularly large space needed to provide the sufficient number of instruments. This negatively impacts the ease of viewing the instruments, especially having small instrument heads. The very small instrument heads with the surgical tools themselves are negative with the cleaning and maintenance process. Two different technical constructions are known, some having a hinge, the others using the elasticity of the material and the distal opening of the tube. The distal end of the interior drive component is formed into two elastic parts to exert the function by pushing them out of the distal opening of the tube to open or by retracting them to close e.g. the jaws of a forceps.

SUMMARY OF THE INVENTION

In accordance to the present invention the disclosed surgical instrument system provides a plurality of interchangeable intrument heads with surgical tools to be easily connected under positive lock-in and disconnected, possibly by one hand holding and later actuating the instrument function, comprising a handgrip with a frame part and a movable trigger part, a tube, projecting forwardly of the handgrip and a shaft, seized to be slidably received in the tube as an interior drive component. The shaft has a distal and forward tie-in point for the interchangeable instrument heads, a second proximal and backward tie-in point along the shaft to be selectively engaged to the movable trigger handle of the handgrip and proximal to the proximal tie-in point a grip as an operating component. The grip is preferably a ring-like or similar material enlargement and projects backwards of the handgrip. The shaft is preferably cylindrical, yet in another embodiment may be squared or have irregular forms. In another embodiment a second proximal tie-in point to be selectively engaged to the moveable trigger handle is present to actuate the distal tie-in point under attachment of one of the plurality of instrument heads.

The distal tie-in point near or at the end of the shaft can have several embodiments. In a preferred embodiment the shaft has a ball-like enlargement or lateral protuberances. The enlargement is introduced into a cavity at one of the the variable instrument heads. The cavity is expandable, having one or more slots. After introduction of the shaft the cavity snaps over it to attach the instrument head tensile resistant to a certain force at the distal shaft. In yet another embodiment the distal shaft has lateral projections, preferably formed like hooks. Accordingly the instrument heads have bifurcation-like projections with bores to snap over the projections of the distal tie-in point to achieve the tensile restistant attachment of the instrument heads. The instrument heads can also have loops of metal or plastic filaments to be fixed at the hooks. In another embodiment the shaft has a circular or partly circular recess or groove as a tie-in point. To achieve the tensile resistant attachment the instrument heads accordingly have one or more hook-like projections to be deflected and to snap into the corresponding recess or groove of the shaft.

The attachment of the instrument head can allow free rotation or a fixed attachment, the instrument head to be rotated with the shaft. Under tensile force the coupling means of the instrument head will be pressed against the inner wall of the tube and its position will positively be fixed for the surgical work. The friction is also increased at the proximal tie-in point when the shaft is under tensile force, which results in a fixed rotation of the shaft.

The proximal and backward tie-in point of the shaft can have several embodiments. In a preferred embodiment a ball-like positive material enlargement is selectively engaged with the movable trigger part of the handgrip by deflecting the shaft with the grip e.g. with the thumb. Accordingly the coupling means of the movable trigger handle extends over the shaft, ending in a bifurcation with a slot to receive the shaft. The slot is additionally enlarged with a lock-in cavity to selectively engage with the proximal tie-in point of the shaft. The bifurcation itself is seized wide enough to slide over the shaft without actuating it when the proximal tie-in point is disconnected.

In yet another embodiment the proximal tie-in point is formed by preferably cylindrical lateral projections such as pivots. Accordingly the coupling means of the movable trigger handle are bifurcations to slidably receive the projections. In another embodiment the shaft has a circular recess or partly circular recesses or grooves. Accordingly the coupling means are formed by symmetrical protuberances within the bifurcation of the movable trigger handle. The proximal tie-in point is seized to be slidably received into the opening of the tube at the side of the handgrip according to the needed distance to locate the distal tie-in point before the shaft to disconnect the instrument head.

In another embodiment the shaft is bended proximal the most proximal tie-in point.

The handgrip consists of a frame part and a movable part as a trigger handle for the actuaction of the instrument head, slidably attached with a screw or simular attachment to the frame part. From the frame part the tube with a predetermined length extends forward. Its opening at the frame part side is a taper bore or a slot to allow the shaft to be deflected to the side. A preferably rubber sealing with a suitable hole for the shaft is attached to the frame part at the area of the shaft opening.

Preferably a predetermined distance is present between the proximal tie-in point and the grip of the shaft to avoid any traction on the shaft, when the proximal tie-in point is disconnected. The deflection to selectively engage the shaft and the trigger handle and the axial movement of the shaft can be done with the thumb of the hand holding the frame part of the handgrip.

The shaft is preferably made of elastic metal materials e.g. stainless steal to deflected to the side, yet having a certain stability to hold the engagement with the movable trigger handle of the handgrip.

The shaft can also be made of plastic material and be used only once. The shaft can wear out under the actuation of the instrument function and through the deflection and can be provided separate from the surgical instrument system.

In another embodiment the grip of the shaft is insulated or made of insulating material and acts as a plug to connect HF energy to the shaft.

The interchangeable instrument heads with the surgical tools are held in a magazine with preferably transparent plug-in receptacles. The receptacles present a guiding part such as a tapered or cylindrical bore to accurately approximate the distal tie-in point of the shaft. This preferably funnel-shaped insertion part acts like an insertion assistance. The instrument heads are held in the plug-in receptacles by a clamp-like mechanism by enlargements at the receptacles, alternatively pins or pivots, which fit into corresponding recesses in the instrument heads. The instrument heads are by these engagement means fixed in the receptacles with a certain force to disconnect it from the shaft, when the distal tie-in point is before the tube to overcome its attachment force to the shaft.

In another embodiment the magazine with the plug-in receptacles including the instrument heads, these however preferably made from stainless steel, are made of plastic material and are intended to be disposable. In yet another embodiment the tube, cracking rather easily because of its small diameter, has an enlargement with a thread to be screwed into the frame part of the handgrip.

BRIEF DESCRIPTION OF THE DRAWINGS

Below, the invention with its essential details is explained in a greater detail based on the drawings.

In the drawings:

FIG. 4 shows the distal tie-in point with a ball-like enlargement with an instrument head with the corresponding coupling means.

FIG. 5 shows the distal tie-in point of a squared shaft with recesses with an instrument head with the corresponding coupling means.

FIG. 6 shows the distal tie-in point with lateral pivots with an instrument head with the corresponding coupling means.

FIG. 10 shows the shaft with distal and proximal tie-in points and a ring-like grip to be used with a surgical instrument.

FIG. 11 shows the shaft with a distal and two proximal tie-in points and a rod-like grip to be used with a surgical instrument.

FIG. 12 shows the part of the shaft with a bend proximal the proximal tie-in point and an axial and insulated grip to be used with a surgical instrument.

FIG. 13 shows the magazine with the transparent receptacles for the interchangeable instrument heads, the insertion funnels or access opening and the locking means for the instrument heads FIG. 14 shows different interchangeable instrument heads with different surgical tools

DETAILED DESCRIPTION OF THE DRAWINGS

Figure 1:
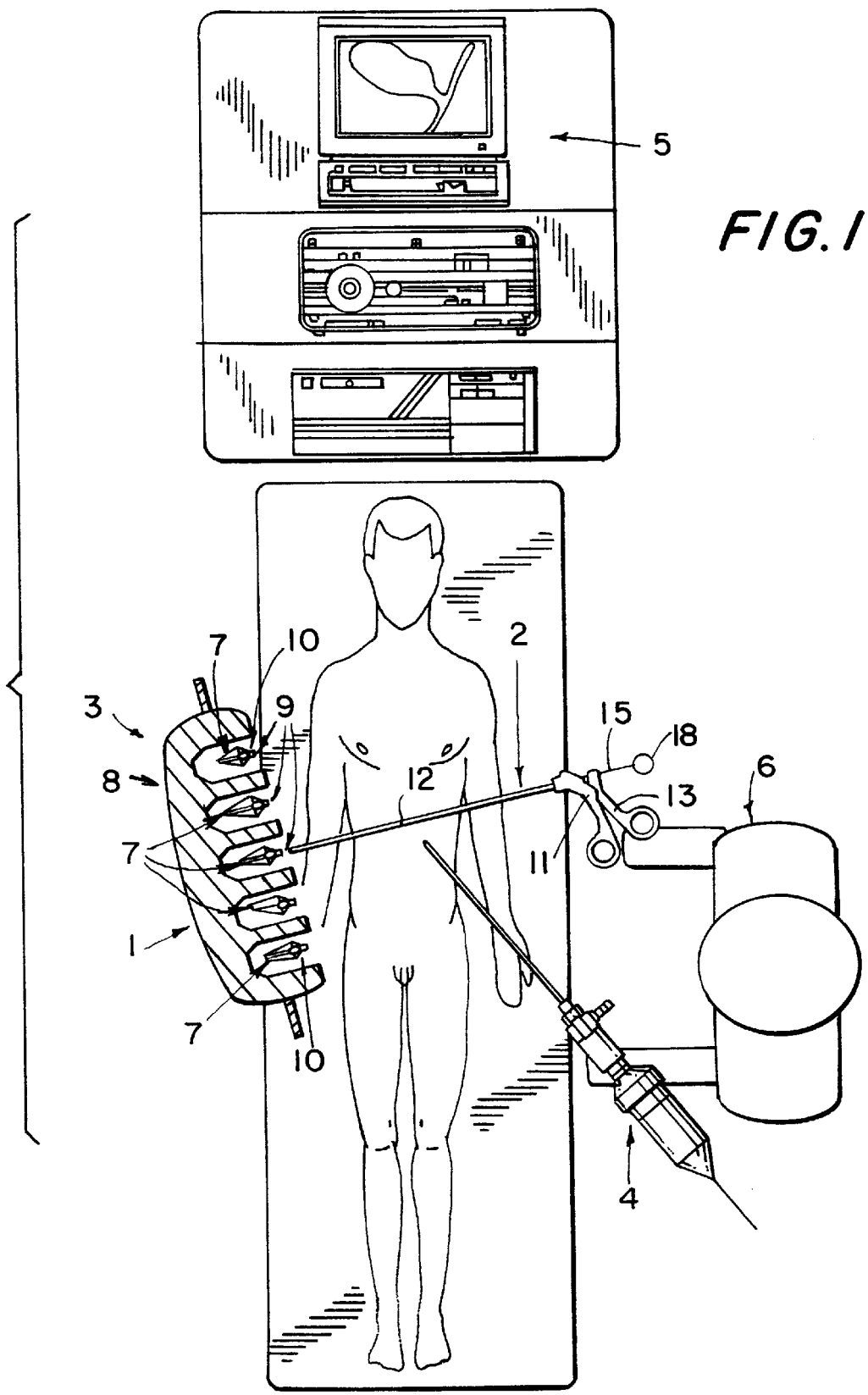
FIG. 1 is an overview of the surgical instrument system, not to scale, of a surgical field with the device pursuant to the invention in use for surgery

FIG. 1 shows surgical instrument system 1, pursuant to the invention, consisting essentially of the surgical instrument holder 2 with tube 12 and handgrip 11 and the shaft 15 and a plurality of interchangeable instrument heads 10 with surgical tools 7, held in receptacles 9 in magazine 8 for use in surgery. This involves surgery under endoscopic control, in which the surgical area is located in the abdominal cavity of the patient, shown via endoscope 4 on the video monitor 5. The position of the video monitor is represented only schematically in FIG. 1 and the surgeon 6 has the possibility of placing monitor 5 in such manner that a favorable angle of view can be set up between the video monitor and the other surgical areas.

Magazine 8 with receptacles 9 pursuant to the invention makes it possible for the surgeon 6 to select and change surgical tools 7 required for the surgery by himself. This can be done with one hand, so that surgeon 6 can, e.g. hold endoscope 4 with the other hand and the surgical assistance otherwise required is no longer necessary.

Magazine 8 has a pre-settable number of plug-in receptacles 9 for interchangeable instrument heads with surgical tools 7. Instrument heads 10 can also include tube 12 or part thereof and being separable from the remaining instrument holder. The instrument holder is essentially formed of tube 12, handgrip 11 and shaft 15 with grip 18 at or near the end of the shaft 15, projecting backward of the handgrip 11.

Figure 2:
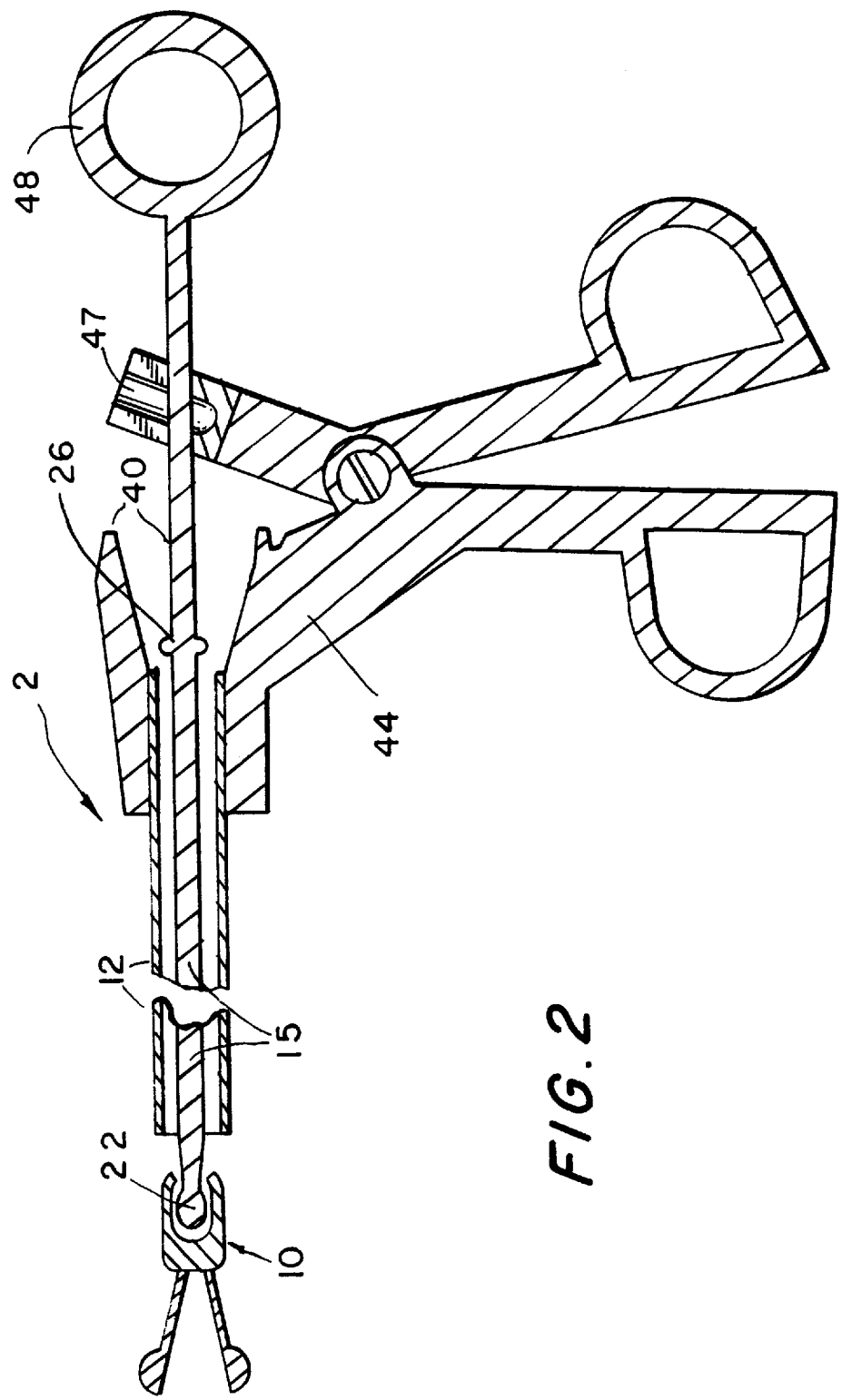
FIG. 2 shows a lateral cross-section of an instrument with the distal locking means before the tube and the proximal engagement means disconnected.

FIG. 2 shows, in a lateral cross-sectional view, surgical instrument holder 2 with the coupling mechanism for separation of a possible instrument head 10 to the shaft 15. The distal tie-in point 22 is positioned forwardly of the tube 12 of holder 2. The proximal tie-in point 26 is within the opening 40 of the tube 12 at the side of the handgrip 44.

Figure 3:
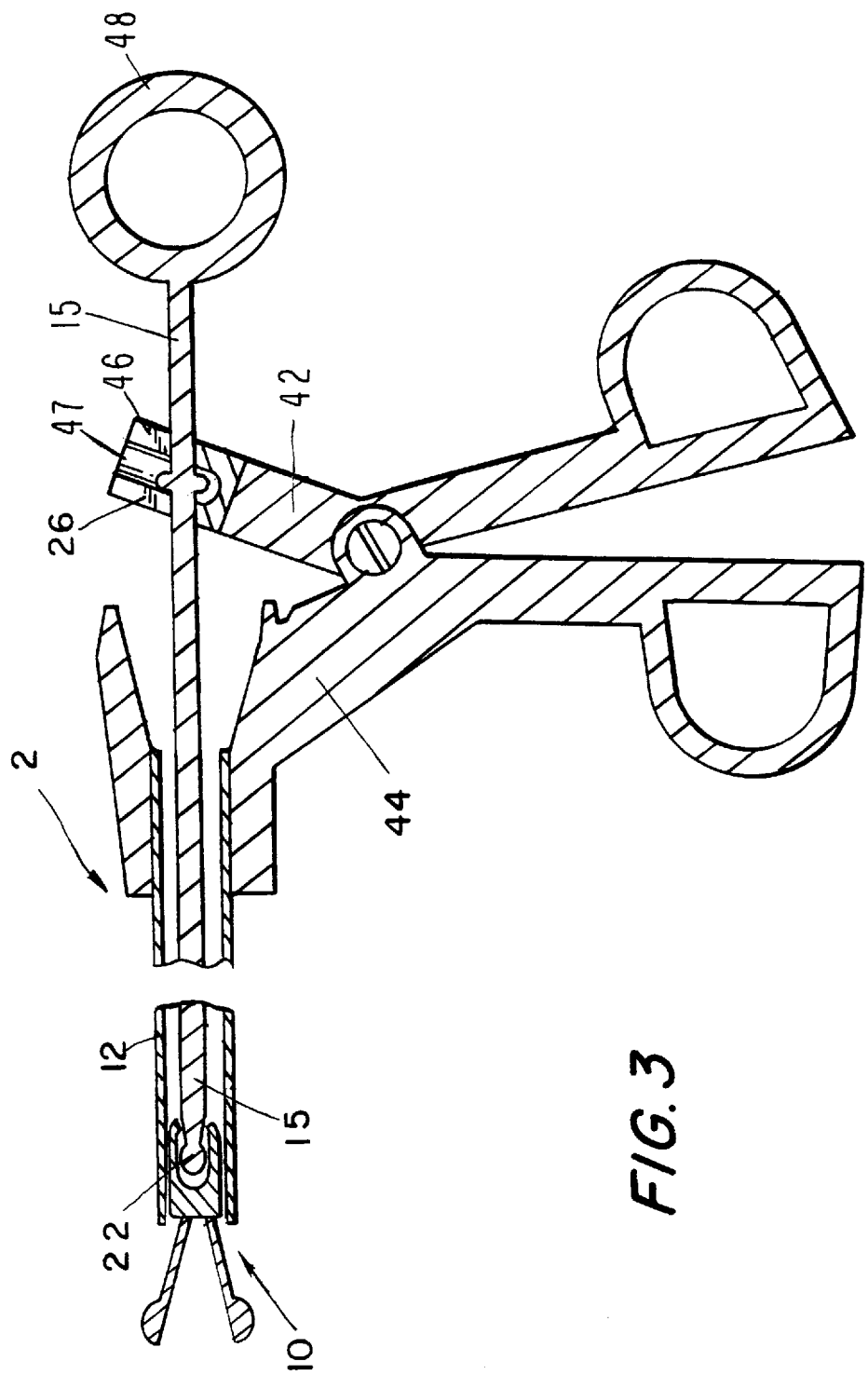
FIG. 3 shows a lateral cross-section of an instrument with the distal tie-in point with an attached instrument head within the tube and the proximal engagement means connected.

FIG. 3 shows, in a lateral cross-sectional view, surgical instrument holder 2 with the distal tie-in point 22 positioned within the tube 12. The proximal tie-in point 26 is connected to the movable trigger handle 42 of handgrip 44. The slot 46 has the cavity 47 to separately engage tie-in point 26 with the movable trigger handle 42. The slot 46 slides over shaft 15 without any engagement, grip 48 is situated in a predetermined distance at end of shaft 15.

FIG. 4 shows the positive material enlargement 50 in the lock-in cavity 52 in material enlargement 53 of instrument head 10 with surgical tool 7.

FIG. 5 shows the recesses 54 in shaft 15. Instrument head 10 with surgical tool 7 has hook-like projections 56.

FIG. 6 shows hook-like lateral pivots 58 at shaft 15. Instrument head 10 with surgical tool 7 has two bifurcation-like projections 60 with bore 62.

Figure 7:
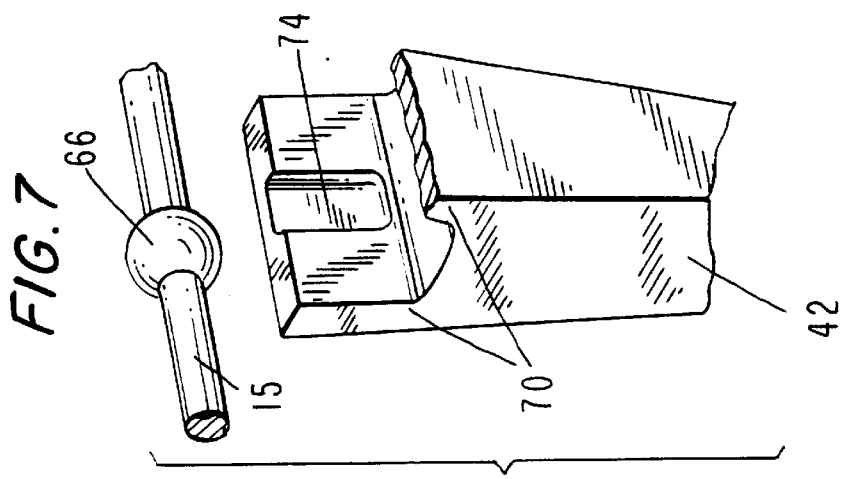
FIG. 7 shows the bifurcation of the movable trigger part of the handgrip with the slot and a lock-in cavity in engagement with the ball-like enlargement of the shaft.

FIG. 7 shows the lateral pivots 65 at the shaft 15. Movable trigger handle 42 has a bifurcation-like slot 70 with symmetrical slots 72.

Figure 8:
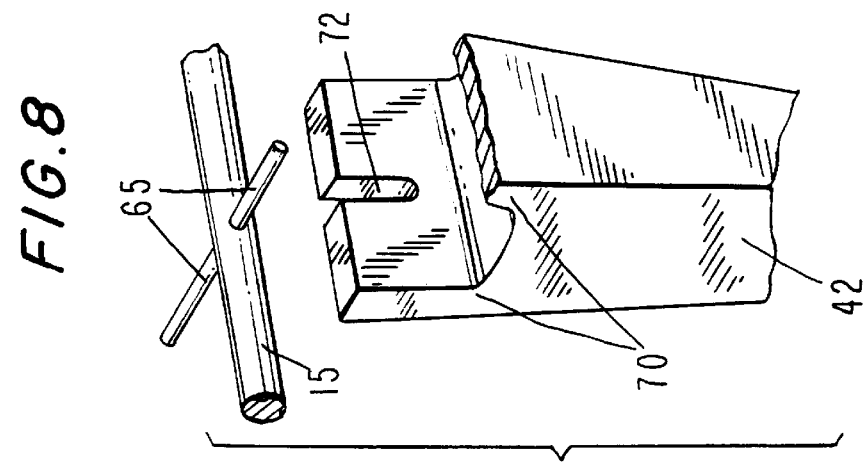
FIG. 8 shows the bifurcation of the movable trigger part of the handgrip with the slot in engagement with the lateral pivots at the shaft.

FIG. 8 shows ball-like enlargement 66 of shaft 15. Movable trigger handle 42 has a bifurcation-like slot 70 with a symmetrical cavity 74.

Figure 9:
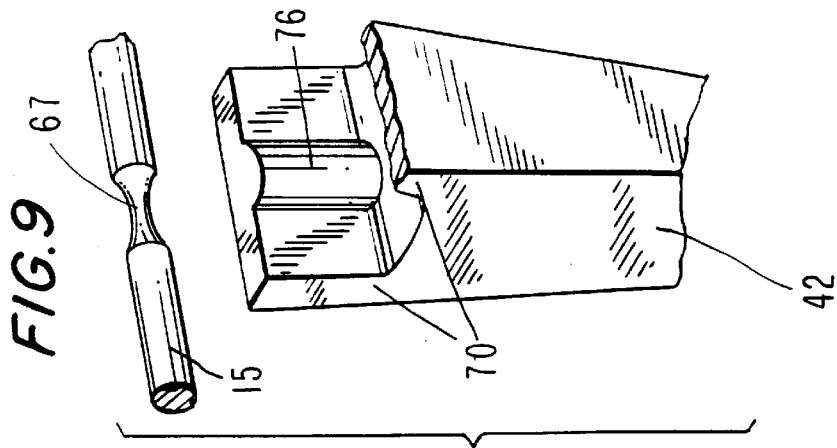
FIG. 9 shows the bifurcation of the movable trigger part of the handgrip with the slot and the symmetrical protuberances within the slot in engagement with the recess of the shaft.

FIG. 9 shows a recess 67 of the shaft 15. Moveable trigger handle 42 has a bifurcation-like slot 70 with a symmetrical enlargement 76.

FIG. 10 shows a shaft 15, to be used with the instrument holder 2 with tube 12 and handgrip 11, with ball-like distal tie-in point 50, the proximal ball-like tie-in point 66 and the ring-like grip 78.

FIG. 11 shows a shaft 15, to be used with the surgical instrument holder 2 with tube 12 and handgrip 11, with a distal tie-in point 22 with recesses 54, two proximal tie-in points with lateral projections 65 along the shaft and a rod-like grip 80.

FIG. 12 shows the proximal part of shaft 15, to be used with the surgical instrument holder 2 with tube 12 and handgrip 11, with a proximal ball-like tie-in point 66, with a bend 81 and a enlargement with an insulation as a grip 82, acting as a plug to connect HF energy via plug 84 to the shaft 15.

FIG. 13 shows magazine 8 with transparent plug-in receptacles 9, hold by pivots 90. An instrument head 10 with surgical tools 7 is fixed in the receptacle 9 by a clamping means 94 with two pivots. Insertion funnel 96 guides the distal tie-in point 22 of shaft 15 to the instrument head. After coupling the instrument head 10 to shaft 15 it is released by lifting tube 12. Transparent cover 92 is then removed.

FIG. 14 shows an instrument head 10 with different surgical tools 7 like e.g. a scalpel 100, blunt forceps 101, sharp forceps 102, needle driver 103. In a preferred embodiment the enlargement 105 has a circular recess or one or more partly circular recesses 107 to engage with the locking means of the receptacle. Additionally the enlargement 105 has an expandable cavity 109 with at least one slot 111 to lockably be tensile attached to the distal tie-in point of the shaft. Hook-like projection 113 or bifurcation-like projections 115 with a bore 116 are as well possible as loops of metal or plastic filaments 117.

One skilled in the art will recognize at once, it would be possible to construct the present invention from a variety of materials. Suitable material include stainless steel and a wide variety of plastics used in the medical field. Preferably the surgical instrument system and the separately provided part are constructed of stainless steel and plastic.

What is claimed is:

1. A surgical instrument which is adapted for passage through a surgical sleeve or cannula into and out of the body cavity of a patient undergoing surgery and is designed for use by a surgeon to perform different tasks in minimal invasive surgery on a patient with the aid of respective ones of a plurality of surgical tools, said instrument comprising:
    (a) an elongated tube having a distal end region and a proximal end region presenting a distal end opening and a proximal end opening, respectively;
    (b) a handgrip having
        (i) a frame part which includes an adjunct fixedly connected to said proximal end region of said tube, said frame part extending generally transversely of said adjunct and said tube, and
        (ii) a movable trigger handle having first and second arm portions and at the juncture between said arm portions being pivotally connected to said frame part, said first arm portion at an end region thereof remote from the pivotal connection between said movable trigger handle and said frame part being further provided with a first coupling means;
    (c) a shaft extending movably through said tube and having a distal end region and a proximal end region,
        (i) said shaft in said distal end region thereof being provided with a distal tie-in point adapted, upon longitudinal movement of said shaft within said tube, to be selectively slidably retracted into and protracted from said tube through said distal end opening of said tube, and
        (ii) said shaft in said proximal end region thereof being provided with at least one proximal tie-in point the most distal one of which is spaced from said distal tie-in point so as to be located adjacent the site of said adjunct of said frame part and proximal of said proximal end opening of said tube when said shaft is moved longitudinally in said tube so as to cause said distal tie-in point to be protracted from said distal end region of said tube, and
        (iii) said shaft adjacent the location of said at least one proximal tie-in point thereon being sufficiently flexible to enable said shaft to be flexed laterally relative to said adjunct of said frame part and said proximal end region of said tube so as to permit said at least one proximal tie-in point to be selectively shifted into or out of operative engagement with said first coupling means, thereby selectively to connect said movable trigger handle drivingly to said shaft via said at least one proximal tie-in point and said first coupling means or to disconnect said shaft from said movable trigger handle;
    (d) each of said plurality of interchangeable instrument heads being provided with a respective second coupling means for enabling a selected instrument head to be connected to said distal end region of said shaft through a rotatable snap-fit between said second coupling means of said instrument head and said distal tie-in point of said shaft, so that upon retraction of said distal tie-in point, along with an instrument head connected thereto via said second coupling means, into said distal end region of said tube through said distal end opening, loosening of said second coupling means and separation of said instrument head and the surgical tool carried thereby from said shaft during the performance of a surgical task are effectively inhibited by said tube; and
    (e) a grip member secured to said shaft at a location along the shaft proximal of the most proximal one of said at least one proximal tie-in point for permitting the surgeon, by appropriately manipulating said grip member with the thumb of the hand holding said frame part of said handgrip, to effect a desired lateral flexing of said proximal end region of said shaft relative to said adjunct of said frame part and relative to the axis of said tube either
        (i) for establishing a driving connection between said trigger handle and said shaft via said first coupling means and said at least one proximal tie-in point of said shaft to enable the associated surgical tool to be operated by manipulation of said trigger handle and the resultant longitudinal movements of said shaft through said tube or
        (ii) for disabling the driving connection between said trigger handle and said shaft by extracting said at least one proximal tie-in point from said first coupling means to enable said shaft to be moved freely longitudinally through said tube by manipulation of said grip member for shifting said distal tie-in point to a location either inside or outside said distal end region of said tube while avoiding any surgical operation of said surgical tool.

2. A surgical instrument according to claim 1 wherein the distal tie-in point of the shaft is formed by a preferably ball-shaped enlargement of the shaft.

3. A surgical instrument according to claim 1 wherein the distal tie-in point is formed by a circular recess or one or more partly circular recesses of the shaft.

4. A surgical instrument according to claim 1 wherein the distal tie-in point is formed by at least one preferably pivot-like lateral protuberance.

5. A surgical instrument according to claim 1 wherein the at least one proximal tie-in point along the shaft is formed by a preferably ball-shaped enlargement of the shaft.

6. A surgical instrument according to claim 1 wherein the at least one proximal tie-in point is formed by a circular recess or one or more partly circular recesses of the shaft.

7. A surgical instrument according to claim 1 wherein the at least one proximal tie-in point is formed by at least one preferably pivot-like lateral protuberance.

8. A surgical instrument according to claim 1 wherein the shaft has two or more proximal tie-in points.

9. A surgical instrument according to claim 1 wherein the grip member is formed by a ring-like enlargement of the shaft.

10. A surgical instrument according to claim 1 wherein the grip is member formed by a rod-like enlargement of the shaft.

11. A surgical instrument according to claim 1 wherein the grip member is formed by a longitudinal enlargement of the shaft.

12. A surgical instrument system according to claim 11 wherein the longitudinal enlargement of the shaft is insulated and acts as a plug to connect HF energy to the shaft.

13. A surgical instrument according to claim 1 wherein the instrument heads have an enlargement with an expandable cavity with at least one slot to couple tensile resistant under positive lock-in, the coupling area being outside or inside the tube.

14. A surgical instrument according to claim 13 wherein the instrument heads have hook-like projections to snap into the recess or recesses of the shaft.

15. A surgical instrument according to claim 14 wherein the instrument heads have a bifurcation-like projection with over to snap ober the lateral protuberances of the shaft.

16. A surgical instrument according to claim 14 wherein the instrument heads have metal or plastic filaments to be attached to the lateral protuberances of the shaft.

17. A surgical instrument according to claim 1 wherein said first coupling means on said first arm portion of the movable trigger handle is formed by a bifurcation-like slot with a cavity.

18. A surgical instrument according to claim 1 wherein said first coupling means on said first arm portion of the movable trigger handle is formed by a bifurcation-like slot with symmetrical slots across the bifurcation.

19. A surgical instrument according to claim 1 wherein said first coupling means on said first arm portion of the movable trigger handle is formed by a bifurcation-like slot with symmetrical protuberances across the bifurcation.

20. A surgical instrument system comprising a surgical instrument according to claim 1 and in combination therewith a magazine provided with a plurality of separate receptacles for holding a number of said interchangeable instrument heads, respectively, each of said receptacles having an access opening in communication with the interior instrument head-receiving space of that receptacle to enable said distal end region of said shaft to be inserted selectively into each of said receptacles, either (a) for bringing said distal end region of said shaft, when the latter does not have an instrument head coupled to said distal tie-in point, into that receptacle so as to establish between a respective instrument head located in that receptacle and said shaft an interlocking engagement of said distal tie-in point of said shaft via said second coupling means with said respective instrument head, thereby to enable that instrument head and its associated surgical tool to be extracted from that receptacle, or (b) for bringing said distal end region of said shaft, when an instrument head is coupled to said distal tie-in point of said shaft, into an unoccupied receptacle, thereby to enable that instrument head to be deposited in said unoccupied receptacle and released from said shaft in conjunction with retraction of said distal end region of said shaft from that receptacle, and wherein the magazine includes third coupling means to attach to said magazine a pre-settable number of receptacles for interchangeable instrument heads.

21. A surgical instrument system according to claim 20 wherein the coupling means of the magazine are pivots to fit into bores in the receptacles.

22. A surgical instrument system according to claim 20 wherein the receptacles have fourth transparent and detachable covers.

23. A surgical instrument system according to claim 1 wherein said third receptacles have coupling means to hold the instrument heads with a certain force to overcome their attachment to the shaft, when the distal tie-in point is outside the tube.

24. A surgical instrument system according to claim 23 wherein said fourth coupling means in the receptacles to hold the instrument heads are pivots.

25. A surgical instrument system according to claim 23 wherein the associated fourth coupling in the receptacles to hold the instrument heads are protuberances at or near the access opening.

26. A surgical instrument according to claim 23 wherein each instrument head has a circular recess or partly circular recesses to let the coupling means of the respective receptacle snap into it.

27. A surgical instrument according to claim 1, wherein the moveable trigger handle of the handgrip is elongated and projects across the shaft in a bifurcation-like slot.

28. A surgical instrument according to claim 27, wherein the bifurcation-like slot of the moveable trigger handle of the handgrip slides over the shaft without engaging it.

29. A surgical instrument according to claim 1 wherein the location of said proximal end opening of said tube in the vicinity of said adjunct of said frame part of the handgrip allows the shaft to be flexed easily.

30. A surgical instrument according to claim 29 wherein said proximal end opening of said tube in the vicinity of said adjunct of said frame part of the handgrip merges into a tapered bore.

31. A surgical instrument according to claim 29 wherein said proximal end opening of said tube in the vicinity of said adjunct of said frame part of the handgrip merges into a conical cavity.

32. A surgical instrument according to claim 29 wherein said proximal end opening of said tube in the vicinity of said adjunct of said frame part of the handgrip merges into a slot.

* * * * *